(12) United States Patent
Koole (10) Patent No.: US 9,274,441 B2
(45) Date of Patent: Mar. 1, 2016

(54) INSPECTION METHOD FOR IMPRINT LITHOGRAPHY AND APPARATUS THEREFOR

(75) Inventor: Roelof Koole, Eindhoven (NL)

(73) Assignee: ASML NETHERLANDS B.V., Veldhoven (NL)

( * ) Notice: Subject to any disclaimer, the term of this patent is extended or adjusted under 35 U.S.C. 154(b) by 500 days.

(21) Appl. No.: 13/812,127

(22) PCT Filed: Jul. 18, 2011

(86) PCT No.: PCT/EP2011/062256
§ 371 (c)(1),
(2), (4) Date: Jan. 24, 2013

(87) PCT Pub. No.: WO2012/022561
PCT Pub. Date: Feb. 23, 2012

(65) Prior Publication Data
US 2013/0120729 A1    May 16, 2013

Related U.S. Application Data

(60) Provisional application No. 61/374,004, filed on Aug. 16, 2010.

(51) Int. Cl.
*G03B 27/52*     (2006.01)
*G03B 27/62*     (2006.01)
(Continued)

(52) U.S. Cl.
CPC ............ *G03F 7/70925* (2013.01); *G01N 21/94* (2013.01); *G03F 7/0002* (2013.01);
(Continued)

(58) Field of Classification Search
CPC .............. G03F 7/7035; G03F 7/70325; G03F 7/70408; G03F 7/703; G03F 7/70858; G03F 7/7085; G03F 7/70866; G03F 7/70908–7/70925; G03F 7/70958; G03F 7/0017; G03F 9/7038; G03F 9/7042; G01N 2021/95676; G01N 21/94
USPC ......... 355/30, 53, 67–71, 72–77, 78, 95, 132; 250/492.1, 492.2, 492.22, 493.1, 548; 430/5, 8, 22, 30, 311, 312
See application file for complete search history.

(56) References Cited

U.S. PATENT DOCUMENTS 4,731,115 A      3/1988   Abkowitz et al.
5,399,867 A *    3/1995   Kohno ........................ 250/461.1
(Continued)

FOREIGN PATENT DOCUMENTS

JP    2007-69217    3/2007
JP    2007-523249   8/2007
(Continued)

OTHER PUBLICATIONS

Japanese Office Action mailed Sep. 30, 2014 in corresponding Japanese Patent Application No. 2013-524395.
(Continued)

*Primary Examiner* — Christina Riddle
(74) *Attorney, Agent, or Firm* — Pillsbury Winthrop Shaw Pittman LLP (57) ABSTRACT

A method is disclosed for inspecting a device imprint lithography template to detect defect particles of imprintable medium remaining on the patterned imprinting surface after an earlier imprint step. The method involves illuminating the patterned surface with radiation of a first wavelength selected to induce fluorescence of the defect particles and not to induce fluorescence of anti-adhesion compound on the patterned surface. The presence of defect particles is indicated by the presence of fluorescence from the patterned surface and can be used to initiate a cleaning step when necessary, speeding processing by eliminating unnecessary cleaning. The elimination of false positives from transferred anti-adhesion compound is reduced or eliminated. Related apparatus is also disclosed.

22 Claims, 3 Drawing Sheets

(51) Int. Cl.
| | | |
|---|---|---|
| *G03B 27/02* | (2006.01) | |
| *G03B 27/04* | (2006.01) | |
| *G03F 7/20* | (2006.01) | |
| *G03F 7/00* | (2006.01) | |
| *G01N 21/94* | (2006.01) | |
| *B82Y 10/00* | (2011.01) | |
| *B82Y 40/00* | (2011.01) | |
| *G01N 21/956* | (2006.01) | |

(52) U.S. Cl.
CPC ........ *G03F7/70908* (2013.01); *G03F 7/70958* (2013.01); *B82Y 10/00* (2013.01); *B82Y 40/00* (2013.01); *G01N 2021/95676* (2013.01)

(56) References Cited

U.S. PATENT DOCUMENTS

| | | | |
|---|---|---|---|
| 5,772,905 A | 6/1998 | Chou | |
| 5,807,632 A * | 9/1998 | Pedginski et al. | 428/352 |
| 6,080,450 A * | 6/2000 | Cantor | 427/517 |
| 6,334,960 B1 | 1/2002 | Willson et al. | |
| 6,500,602 B1 * | 12/2002 | Magnitakil et al. | 430/321 |
| 7,087,907 B1 * | 8/2006 | Lalovic et al. | 250/461.1 |
| 7,304,310 B1 | 12/2007 | Shortt et al. | |
| 8,294,889 B2 * | 10/2012 | Kashiwagi et al. | 356/237.2 |
| 8,357,536 B2 * | 1/2013 | Wuister | 436/5 |
| 2003/0205658 A1 * | 11/2003 | Voisin | 249/187.1 |
| 2003/0215747 A1 * | 11/2003 | Kim et al. | 430/284.1 |
| 2004/0124566 A1 | 7/2004 | Sreenivasan et al. | |
| 2004/0189972 A1 * | 9/2004 | Mulkens et al. | 355/71 |
| 2005/0008944 A1 * | 1/2005 | Cerrina | B82Y 10/00 430/5 |
| 2005/0116370 A1 | 6/2005 | Ogino et al. | |
| 2005/0236360 A1 * | 10/2005 | Watts et al. | 216/41 |
| 2005/0274693 A1 | 12/2005 | Heidari et al. | |
| 2007/0053867 A1 | 3/2007 | Ober et al. | |
| 2007/0264591 A1 * | 11/2007 | Wuister et al. | 430/269 |
| 2009/0028910 A1 * | 1/2009 | DeSimone et al. | 424/401 |
| 2009/0263750 A1 | 10/2009 | Maeda | |
| 2011/0043795 A1 * | 2/2011 | Den Boef et al. | 356/237.2 |
| 2011/0272382 A1 * | 11/2011 | Owa et al. | 216/37 |
| 2012/0127467 A1 | 5/2012 | Ivanov et al. | |

FOREIGN PATENT DOCUMENTS

| | | |
|---|---|---|
| JP | 2007-296823 | 11/2007 |
| JP | 2008-517480 | 5/2008 |
| JP | 2010-8299 | 1/2010 |
| JP | 2010-91295 | 4/2010 |
| JP | 2011-053013 | 3/2011 |
| JP | 2012-26977 | 2/2012 |
| JP | 2013-501228 | 1/2013 |
| KR | 10-0740161 | 7/2007 |
| WO | 02/29883 | 4/2002 |
| WO | 02/067055 | 8/2002 |
| WO | 2004/008125 | 1/2004 |
| WO | 2005/026837 | 3/2005 |
| WO | 2005/031397 | 4/2005 |
| WO | 2009/153926 | 12/2009 |
| WO | 2010/087318 | 8/2010 |
| WO | 2011/015412 | 2/2011 |

OTHER PUBLICATIONS

International Search Report mailed Oct. 13, 2011 in corresponding International Patent Application No. PCT/EP2011/062256.

F.A. Houle et al., "Antiadhesion considerations for UV nanoimprint lithography," Applied Physics Letters, vol. 90, No. 213103, pp. 213103-1-213103-3 (2007).

D. Truffier-Boutry et al., "Chemical degradation of fluorinated antisticking treatments in UV nanoimprint lithography," Applied Physics Letters, vol. 94, No. 044110, pp. 044110-1-044110-3 (2009).

Jan Haisma et al., "Mold-assisted nanolithography: A process for reliable pattern replication," J. Vac. Sci. Technol. B, vol. 14, No. 6, pp. 4124-4128 (Nov./Dec. 1996).

Japanese Office Action mailed Jan. 6, 2014 in corresponding Japanese Patent Application No. 2013-524395.

Taiwan Office Action dated Jan. 17, 2014 in corresponding Taiwan Patent Application No. 100127110.

International Preliminary Report on Patentability and Written Opinion mailed Feb. 28, 2013 in International Patent Application No. PCT/EP2011/062256.

\* cited by examiner

INSPECTION METHOD FOR IMPRINT LITHOGRAPHY AND APPARATUS THEREFOR

CROSS-REFERENCE TO RELATED APPLICATIONS

This application is the U.S. national phase entry of International Patent Application No. PCT/EP2011/062256, filed Jul. 18, 2011, which claims the benefit of priority from U.S. provisional application 61/374,004, which was filed on Aug. 16, 2010 and which is incorporated herein in its entirety by reference.

FIELD

The present invention relates to an imprint lithography inspection method and apparatus. In particular it relates to a method and apparatus for inspection for defects on patterned surfaces of imprint templates.

BACKGROUND

In lithography, there is an ongoing desire to reduce the size of features in a lithographic pattern in order to increase the density of features on a given substrate area. In photolithography, the push for smaller features has resulted in the development of technologies such as immersion lithography and extreme ultraviolet (EUV) lithography, which are however rather costly.

A potentially less costly road to small features (e.g., nanometer sized features) that has gained increasing interest is so-called imprint lithography, which generally involves the use of a "stamp" (often referred to as an imprint template or an imprint lithography template) to transfer a pattern onto a substrate. An advantage of imprint lithography is that the resolution of the features is not limited by, for example, the emission wavelength of a radiation source or the numerical aperture of a projection system. Instead, the resolution is mainly limited to the pattern density on the imprint lithography template.

Imprint lithography involves the patterning of an imprintable medium on a surface of a substrate to be patterned. The patterning may involve bringing together a patterned surface of an imprint lithography template and a layer of imprintable liquid medium (e.g., moving the imprint lithography template toward the imprintable medium, or moving the imprintable medium toward the imprint lithography template, or both) such that the imprintable medium flows into recesses in the patterned surface and is pushed aside by protrusions on the patterned surface. The recesses define pattern features of the patterned surface of the imprint lithography template. Typically, the imprintable medium is flowable when the patterned surface and the imprintable medium are brought together. Following patterning of the imprintable medium, the imprintable medium is suitably brought into a non-flowable or frozen state (i.e. a fixed state), for example by illuminating the imprintable medium with actinic radiation such as UV radiation. The patterned surface of the imprint lithography template and the patterned imprintable medium are then separated. The substrate and patterned imprintable medium are then typically processed further in order to pattern or further pattern the substrate. The imprintable medium may be provided in the form of droplets (e.g. deposited by ink jet printing) on the surface of a substrate to be patterned, but may alternatively be provided using spin coating or the like.

In some instances, imprint lithography may be used to imprint a pattern onto a substrate which has previously received a pattern (or more than one pattern). Where this is the case, it is desirable to align the patterned surface of the imprint template with the pattern already present on the substrate. One known way in which this may be achieved uses alignment marks provided on the imprint template and on the substrate. The relative positions of the imprint template alignment marks and the substrate alignment marks are measured using one or more detectors. The substrate (and/or the imprint template) is then moved with respect to the imprint template (and/or with respect to the substrate) until the substrate and the imprint template are aligned with respect to each other.

SUMMARY

Extraneous particulate matter on the patterned surface of the imprint template may adversely affect the resulting product. Particulate matter present on the patterned surface before imprint is likely to distort features in the pattern formed in the resulting patterned imprintable medium.

With repeated patterning using a patterned surface of an imprint template, particles of hardened or cured imprintable medium may adhere to the patterned surface after the imprint template has become separated from the frozen or solidified patterned imprintable medium. For instance, an adhering defect particle may be in the form of a plug of material remaining inside a recess feature of the patterned surface after separation of the imprint template and the patterned medium, leading to the absence of a protrusion feature on the patterned medium. This plug may exactly fill the recess (for instance, where a protrusion feature has been ripped off from the patterned medium and remains in the recess, leaving a residual, background layer of patterned medium in place on the substrate), or the plug may protrude from the recess (for instance, where part or all of the residual layer of patterned medium underneath the feature on the substrate has also come away with the protrusion feature).

Because the recess on the patterned surface of the imprint template is now already filled with hardened imprintable medium, when the patterned surface is used in a subsequent imprint lithography step, instead of forming the desired protrusion feature, either no feature may be formed (where the recess is filled by the rip-off plug) or an indent feature may be formed instead of a protrusion feature (where the plug is protruding from the recess). Hence, errors may be carried through to subsequent imprint steps effected using the imprint template.

In order to reduce risk of adhesion of undesired particles of imprintable medium to the patterned surface of the imprint template, the imprintable medium may comprise an anti-adhesion compound as a formulation component or the imprint template may have an anti-adhesion compound surface provided thereon. The anti-adhesion compound will typically be at the imprinted surface of the imprintable medium as an anti-adhesion layer and act to provide a low adhesion surface so that the likelihood of undesired adhesion of solidified imprintable medium as defect particles on the patterned surface of the imprint template is reduced. For instance, this may be achieved by the anti-adhesion compound being surface active. Anti-adhesion compounds include fluoroaliphatic polymeric esters with a structure $R_1R_2$, with $R_1$ being $H(OCH_2CH_2)_x$ and $R_2$ being a $(CF_2CF_2)_y CF_3$ group with x and y from 1 to 15. Examples of such materials are ZONYL FSO-100 from DUPONT or FC-4432 from 3M. These anti-adhesion molecules adhere to the silica by strong van der Waals interactions between the $R_1$ moiety and a silica surface of a patterned template. Other anti-adhesion molecules may bind covalently to the template surface, examples of which are fluoroalkyltrichlorosilanes (such as Cytonix FSD 4500, Houle et al, Applied Physics Letters 90 213103, 2007), fluoroalkyltrimethoxysilanes (such as Optool DSX or 1H,1H,2H,2H-perfluorooctyltrimethoxysilane (F13-TMS, from ABCR); Truffier-Boutry et al., Applied Physics Letters 94, 044110 2009). The anti-adhesion compound may transfer or be provided as individual molecules or as a molecular layer, such as a monolayer, onto the patterned surface of the template. Such transfer or provision of anti-adhesion compound is not problematic.

Inspection and cleaning of a patterned surface of an imprint template prior to a further imprint being made may be a significant part of the handling process in order to avoid proliferation of defects caused by adhered particles of solidified imprintable medium. It is desirable to only clean the patterned surface when necessary in order to improve processing speed, and hence inspection is desirable in order to determine when the patterned surface had defect particles for removal.

The patterned surface of an imprint template may be inspected by means of an optical radiation scattering technique. However, a patterned surface will scatter radiation in much the same way as an undesired defect particle. The pattern of the patterned surface may be arbitrary (i.e. non-periodic), and so there may be no way to distinguish a defect particle from the pattern of the patterned surface by simply analyzing scattered radiation. A reference may be required with such scattering techniques, either patterned surface-to-patterned surface, or patterned surface-to-database. This may result in an inspection tool that is expensive and/or relatively slow.

Hence, there is a need to provide a method and apparatus for use in detecting defect particles on a patterned surface of an imprint template for use in imprint lithography for device manufacture. It is desirable that the method and apparatus should be effective with conventional imprintable media, such as a UV-curable photoresist, without the need to substantially modify their compositions. It is desirable that the method and apparatus should be substantially non-invasive, and non-contact so that the processing rate is not substantially reduced.

It is desirable, for example, to provide a method and apparatus to detect defect particles on a patterned surface of an imprint template for use in imprint lithography for device manufacture which reduces or eliminates one or more problems associated with inspection methods and apparatuses in the art. It is desirable, for example, to provide a method and apparatus where the presence of an anti-adhesion compound does not substantially interfere with detection of defect particles.

According to an aspect of the invention, there is provided a method of inspecting a patterned surface of an imprint template for use in imprint lithography of an imprintable medium on a substrate, wherein the imprintable medium or the imprint template comprises an anti-adhesion compound, the method comprising:

illuminating the patterned surface with radiation of a first wavelength such that fluorescence of defect particles of imprintable medium present on the patterned surface induced to yield radiation of a second wavelength, and using the radiation of the second wavelength as an indication of the presence of defect particles of imprintable medium on the patterned surface, wherein the radiation of the first wavelength induces fluorescence of the radiation of the second wavelength from the imprintable medium and does not substantially induce fluorescence of radiation of the second wavelength from the anti-adhesion compound.

The imprintable medium may be any suitable medium which is capable of flow into recesses in the patterned surface and is pushed aside by protrusions on the patterned surface. The recesses define pattern features of the patterned surface of the imprint template. Typically, the imprintable medium is flowable as the patterned surface and the imprintable medium are brought together. The imprintable medium is capable of being brought into a non-flowable or frozen state, also referred to as a cured state, prior to the patterned surface of the imprint template and the patterned imprintable medium being separated. This may, for instance, be achieved by curing the imprintable medium with actinic curing radiation, such as UV radiation. The imprintable medium is typically formed from droplets (e.g. deposited by ink jet printing) on the surface of a substrate to be patterned.

The substrate may be any substrate upon which imprint lithography for device manufacture is useful, such as a semiconductor substrate.

The term "fluorescent" or similar terms, applied to a compound or molecule, means emitting radiation at a second wavelength when excited by a radiation of a first wavelength.

In an embodiment, the first wavelength should have a wavelength that is sufficiently longer than any curing actinic radiation, such as UV radiation, used for any curing of the imprintable medium, in order to avoid unintentional hardening of uncured imprintable medium elsewhere within a lithography apparatus.

In an embodiment, the radiation of the first wavelength does not substantially induce fluorescence of radiation from the anti-adhesion compound, e.g., does not induce fluorescence of radiation of any wavelength therefrom.

The term "wavelength" as used herein may be used to mean a range of wavelengths as well as a single wavelength.

In an embodiment, the method may comprise detecting the radiation of the second wavelength with a detector wherein the detector is arranged to transmit a signal to a processor arranged to initiate cleaning of the patterned surface when the amount of radiation of the second wavelength detected exceeds a threshold value. For instance, a charge coupled device (CCD) or a photomultiplier may be useful as the detector.

The radiation of the second wavelength may be shone onto the patterned surface of the imprint template directly, or it may pass through the imprint template to reach the internal face of the patterned surface.

The emitted radiation of the second wavelength may be collected by a detector positioned for direct collection from the patterned surface or arranged to collect radiation passing through the imprint template from the internal face of the patterned surface.

With such configurations, the imprint template should be of a material substantially transparent or translucent to radiation of the first and second wavelengths.

The detector may be arranged to measure the intensity of detected radiation of the second wavelength and not of the first wavelength. A filter may be positioned between the detector and the patterned surface, wherein the filter is arranged to permit passage of radiation of the second wavelength, and prevent passage of radiation of the first wavelength, to the detector.

In an embodiment, the anti-adhesion compound is a fluoroaliphatic polymeric ester, such as FC-4432 (from 3M company). The first wavelength may be 425 nm or greater.

The imprintable medium may comprise a UV-curable monomer and an initiator compound. In other words, the imprintable medium may be a UV-curable imprintable medium. The initiator compound is thought to generate free radicals when illuminated by UV radiation, these radicals initiating polymerization of the UV-curable monomer.

The UV-curable imprintable medium, when cured, suitably exhibits fluorescence to emit radiation at the second wavelength when illuminated with radiation of the first wavelength. For instance, a suitable UV-curable imprintable medium comprises an acryloyl group (including substituted acryloyl groups) such as an acrylate group (including substituted acrylate groups) or vinyl ether group.

In an embodiment, the initiator compound is selected from a group of initiator compounds exhibiting fluorescence of radiation at the second wavelength when illuminated with radiation of the first wavelength.

In an embodiment, the imprintable medium may comprise a dye adapted to fluoresce radiation at the second wavelength when excited with radiation of the first wavelength.

In other words, there is provided a method of detecting defect particles of imprintable medium on a patterned surface of an imprint template for imprint lithography of the imprintable medium on a substrate, the imprintable medium or the imprint template comprising an anti-adhesion compound, the method comprising illuminating the patterned surface with radiation of a first wavelength selected to induce fluorescence of the defect particles and not to induce fluorescence of anti-adhesion compound, wherein the presence of defect particles is indicated by the presence of fluorescence from the patterned surface.

According to an aspect of the invention, there is provided an imprint lithography template inspection apparatus comprising a source of radiation of a first wavelength configured to illuminate a patterned surface of an imprint template, a detector assembly comprising a detector configured to detect the intensity of radiation of a second wavelength emitted from the patterned surface and a processor configured to initiate cleaning of the patterned surface when the intensity of radiation of the second wavelength exceeds a threshold value, wherein the first wavelength is 425 nm or more and the second wavelength is greater than the first wavelength.

According to an aspect of the invention, there is provided an imprint lithography apparatus comprising the imprint lithography template inspection apparatus above.

The optional features set out herein for any of the aspects of the invention are applicable, either individually or in combination where appropriate, to any other aspects of the invention as set out herein.

BRIEF DESCRIPTION OF THE DRAWINGS

Specific embodiments of the invention will be described with reference to the accompanying figures, in which.

DETAILED DESCRIPTION

Figure 1A:
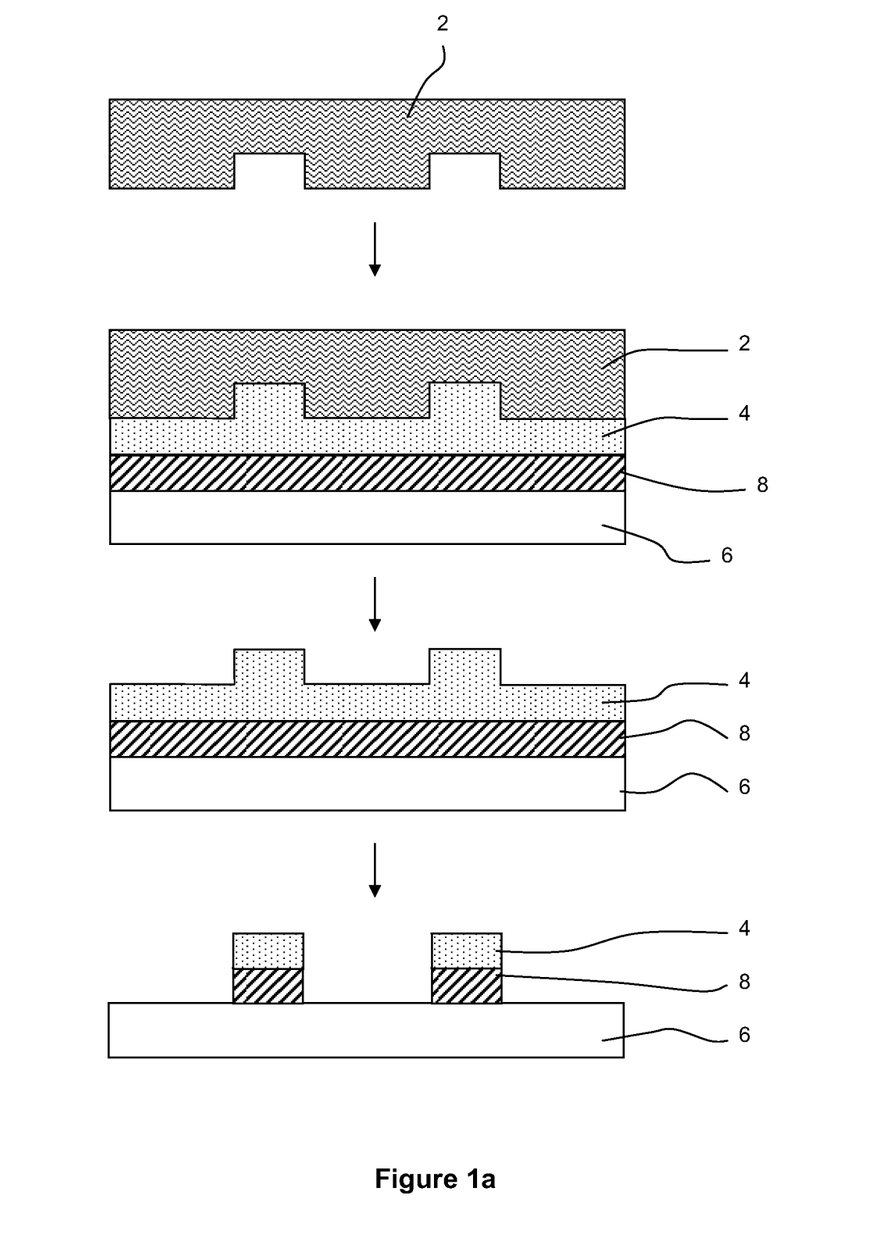
FIGS. 1a and 1b schematically depict examples of, respectively, hot imprint, and UV imprint lithography.
Figure 1B:
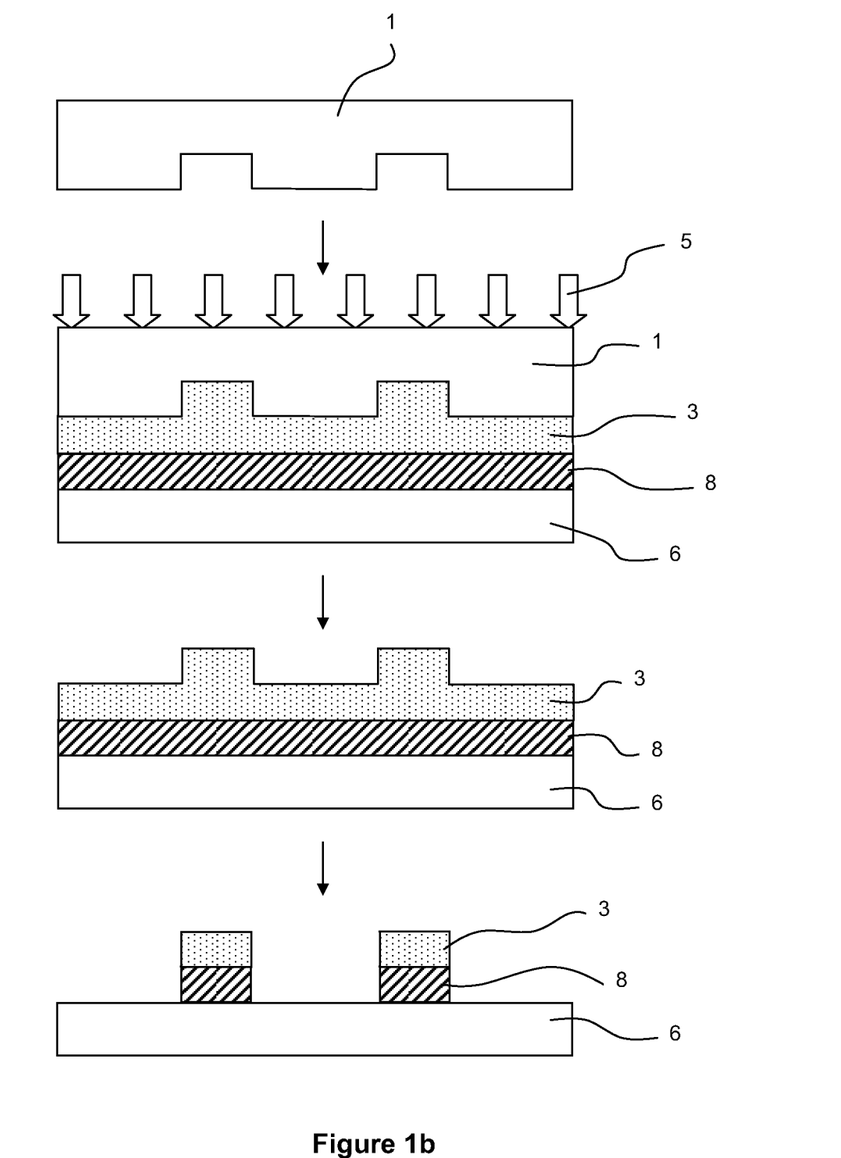

Examples of approaches to imprint lithography are schematically depicted in FIGS. 1a to 1b.

FIG. 1a shows an example of so-called hot imprint lithography (or hot embossing). In a typical hot imprint process, a template 2 is imprinted into a thermosetting or a thermoplastic imprintable medium 4, which has been cast on the surface of a substrate 6. The imprintable medium 4 may be, for example, resin. The resin may, for instance, be spin coated and baked onto the substrate surface or, as in the example illustrated, onto a planarization and transfer layer 8 of the substrate 6. When a thermosetting polymer resin is used, the resin is heated to a temperature such that, upon contact with the template, the resin is sufficiently flowable to flow into the pattern features defined on the template. The temperature of the resin is then increased to thermally cure (crosslink) the resin so that it solidifies and irreversibly adopts the desired pattern. The template 2 may then be removed and the patterned resin cooled. In hot imprint lithography employing a layer of thermoplastic polymer resin, the thermoplastic resin is heated so that it is in a freely flowable state immediately prior to imprinting with the template 2. It may be necessary to heat a thermoplastic resin to a temperature considerably above the glass transition temperature of the resin. The template is pressed into the flowable resin and then cooled to below its glass transition temperature with the template 2 in place to harden the pattern. Thereafter, the template 2 is removed. The pattern will consist of the features in relief from a residual layer of the imprintable medium which may then be removed by an appropriate etch process to leave only the pattern features. Examples of thermoplastic polymer resins used in hot imprint lithography processes are poly(methyl methacrylate), polystyrene, poly(benzyl methacrylate) or poly(cyclohexyl methacrylate). For more information on hot imprint, see e.g. U.S. Pat. No. 4,731,155 and U.S. Pat. No. 5,772,905.

FIG. 1b shows an example of UV imprint lithography, which involves the use of a transparent or translucent template which is transmissive to UV and a UV-curable liquid as imprintable medium (the term "UV" is used here for convenience but should be interpreted as including any suitable actinic radiation for curing the imprintable medium). UV curable liquids are often less viscous than the thermosetting and thermoplastic resins used in hot imprint lithography and consequently may move much faster to fill template pattern features. A quartz imprint template 1 is applied to a UV-curable imprintable medium 3 in a similar manner to the process of FIG. 1a. However, instead of using heat or temperature cycling as in hot imprint, the pattern is solidified by curing the imprintable medium 3 with UV radiation 5 that is applied through the quartz imprint template 1 onto the imprintable medium 3. After removal of the template 1, the imprintable medium 3 is etched. A particular manner of patterning a substrate through UV imprint lithography is so-called step and flash imprint lithography (SFIL), which may be used to pattern a substrate in small steps in a similar manner to optical steppers conventionally used in IC manufacture. For more information on UV imprint, see e.g. U.S. Patent Application Publication No. 2004-0124566, U.S. Pat. No. 6,334,960, PCT Patent Application Publication No. WO 02/067055, and the article by J. Haisma entitled "Mold-assisted nanolithography: A process for reliable pattern replication", J. Vac. Sci. Technol. B14(6), November/December 1996.

Combinations of the above imprint techniques are possible. See, for instance, U.S. Patent Application Publication No. 2005-0274693, which mentions a combination of heating and UV curing an imprintable medium.

Figure 2A:
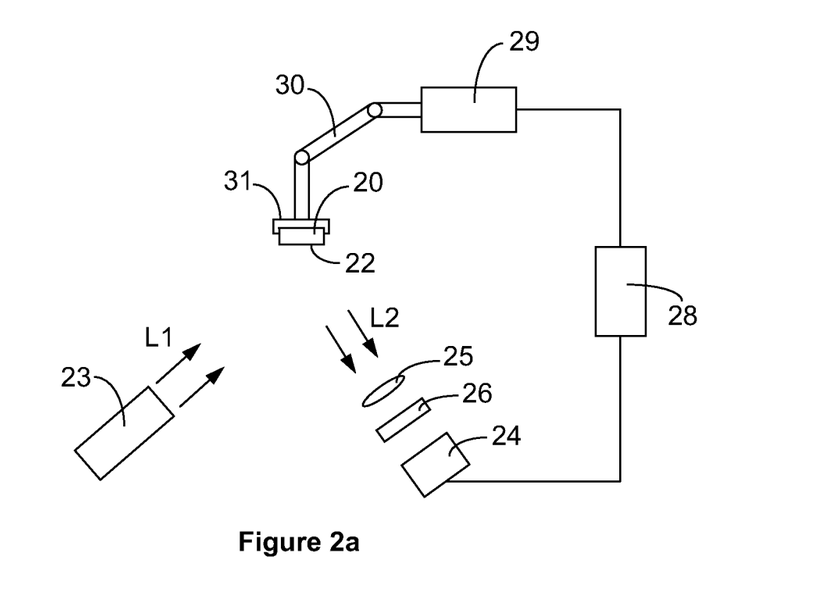
FIGS. 2a and 2b show a schematic view of an imprint lithography inspection apparatus according to an embodiment of the invention and suitable for putting the a method according to an embodiment of the invention into effect.
Figure 2B:
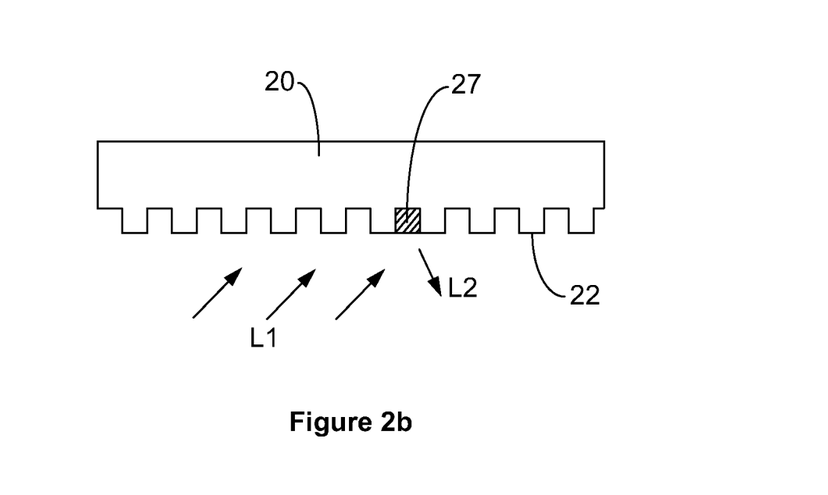

FIGS. 2a and 2b show schematic view of an imprint lithography inspection apparatus according to an embodiment of the invention and suitable for putting the method of an embodiment of the invention into effect.

A radiation output 23 (e.g., a radiation source), e.g., a laser or connected to a laser, is arranged to illuminate the patterned surface 22 of a lithography imprint template 20 with radiation of wavelength L1 in order to excite any defect particles of imprintable medium 27 remaining on or in the patterned surface from a previous imprint lithography step. A detector 24, for instance a charge coupled device or photomultiplier, is positioned to collect radiation of wavelength L2 fluorescent from defect particles on the patterned surface. A lens arrangement 25 is used to collect fluorescent radiation of wavelength L2 and a filter 26 is positioned to prevent the excitation radiation, of wavelength L1, which may be scattered or reflected from the surface, from reaching the detector. In an embodiment, the detector is positioned so that radiation of L1 specularly reflected from the surface misses the detector capture path. Another means to separate a signal arising from excitation radiation L1 from a signal arising from fluorescence radiation L2 is in the temporal domain. For instance a pulsed laser with pulses in the order of picoseconds and a gated detector that only measures in between the excitation pulses may be employed. Typically the total decay rate of fluorescence from the imprintable medium is in the order of nanoseconds, so gating is suitably performed on that timescale.

The imprint template is held in a template holder 31 operably connected by a robot arm 30 to an actuator 29 so that the position of the template may be controlled through a controller 28 driving the actuator. The controller 28 receives a signal from the detector 24 and may be instructed through a computer program.

The inspection according to an embodiment of the method will typically be carried out between individual imprint steps, with the imprint template 20 positioned away from any substrate to be provided with an imprinted medium.

In use, if the detector 24 receives radiation of wavelength L2 sufficient to indicate the presence of one or more defect particles of imprintable medium on the patterned surface 22 of the imprint template 20, then a signal sent from the detector 24 to controller 28 will lead to the actuator 29 being instructed to move the imprint template 20 to a cleaning station (not shown) where the defect particles are removed. Suitable cleaning techniques include but are not limited to application of a cleaning fluid, liquid and/or gas, for instance oxygen, plasma cleaning, ultrasonic cleaning, mechanical wiping, cleaning with a foil, UV exposure, high temperature application or combinations thereof.

After the patterned surface has been cleaned, the controller 28 instructs the actuator 29 to return the imprint template 20 to a position ready for carrying out the next imprint lithography operation. In the case of a carousel-type setup, such as disclosed in PCT patent application publication no. WO2005/026837 a second template may replace a first template while the first template is subjected to inspection and/or cleaning so that imprint lithography may proceed in a substantially uninterrupted manner during inspection and/or cleaning.

The presence of anti-adhesion compound (e.g., within the imprintable medium), present in order to reduce risk of adhesion between the patterned surface and the solidified imprintable medium, may lead to a molecular layer, such as at least a monolayer, of anti-adhesion compound being present on the patterned surface 22 (e.g., after imprint lithography has been once effected with the imprint template 20). In the method and apparatus of an embodiment of the invention, the excitation wavelength L1 is chosen to be such that no substantial fluorescence of wavelength L2, or of any wavelength, takes place as a result of exciting the anti-adhesion compound, so that the presence of the anti-adhesion compound, does not lead to false indication of defect particles 27 and consequently does not lead to unnecessary delay to the process by causing unnecessary cleaning of the patterned surface 22 to be instructed.

For instance, a typical anti-adhesion compound used in or with UV-curable resists is a fluoroaliphatic polymeric ester such as FC-4432 (from 3M Company). This exhibits fluorescence when excited with radiation having a wavelength from say 300 to 425 nm, with the fluorescently emitted radiation red-shifted to a wavelength in the range 400 to 600 nm. This wavelength region within which excitation of a compound results in fluorescence is referred to as the excitation band herein. The peak in the excitation spectrum is at about 380 nm (for fluorescence measured at 460 nm) with the peak in fluorescent intensity at about 450 nm (with excitation at 375 nm). The quantum efficiency (i.e. number of photons fluorescently emitted/number of photons absorbed) of the anti-adhesion compound is in the order of 0.05%.

For initiators used in UV curable photoresists suitable for use as imprintable media for imprint lithography, shorter wavelengths, such as wavelengths less than 425 nm, do not generally induce fluorescence. It is thought that this may be due to the nature of initiators being capable of rupture into free radicals when excited with photons of sufficiently high energy. For wavelengths longer than 425 nm, the photon energy is thought to be insufficient to induce radical formation, and instead, fluorescence is induced with a peak in the excitation spectrum at about 450 nm (emission measured at 510 nm), with the maximum intensity for the red-shifted fluorescence being at about 475 nm (for Irgacure™819 measured at 435 nm excitation). The excitation band of Irgacure™819 is relatively narrow (425 nm to 475 nm). The quantum efficiency of the Irgacure™819 initiator is approximately 0.5%. Other initiators such as Irgacure™369 and Irgacure™184 gave peaks in the excitation spectrum at 410 nm and 400 nm respectively (but with a lower quantum efficiency, by a factor of 5 to 10 compared to Irgacure™819).

For cured acrylate polymers (i.e. the typical polymers derived from a acryloyl monomer such as an acrylate monomer), the peak in the emission spectrum is at about 550 nm when excited at 500 nm. The excitation band of a cured acrylate is broad (575 nm and smaller wavelengths).

Hence, an embodiment of the invention may be put into effect by selection of an excitation wavelength L1 which induces no, or a negligible amount of, fluorescence from the anti-adhesion compound but at which the fluorescence induced from the imprintable medium (e.g., the initiator and/or cured imprintable medium) is adequate for defect particle detection. In other words, the selected excitation wavelength L1 should be outside the range of the excitation band of anti-adhesion layer molecules, but within the range of the excitation band of the imprintable medium (e.g., the initiator and/or cured imprint medium).

For instance, for the anti-adhesion compound FC-4432 (from 3M Company) this value of wavelength L1 should be 425 nm or more. In order to improve the efficiency, the initiator compound may be selected to be an initiator compound which provides fluorescence at the wavelength L2, when excited with the radiation of wavelength L1, so that this additional fluoresced radiation will supplement the radiation fluoresced by the cured polymer present.

The presence of defect particles is indicated by the presence of fluorescence from the patterned surface and can be used to initiate a cleaning step only when necessary, speeding processing by eliminating unnecessary cleaning and reducing any possible damage that each cleaning step may introduce to a minimum. The elimination of false positives from anti-adhesion compound is reduced or eliminated.

An embodiment of the invention provides an advantage over a conventional imprint lithography inspection apparatus and method in that it generates the radiation needed to detect particles at the spot where it is needed, namely from the defect particle itself. The radiation is generated by a moiety already present in the imprintable medium (e.g., a monomer of the imprintable medium or an initiator compound of the imprintable medium), and so may require no modification of known imprintable media, such as by deliberate addition of molecules comprising a fluorophore. This means that the characteristics of the imprintable medium may be left unmodified. However, the scope of the invention does not exclude the deliberate addition of a fluorophore to an imprintable medium, for instance by adding suitable dye.

The imprint template 20 may, for example, have a patterned area for imprint lithography on the patterned surface 22 which measures 25×25 mm or 26×32 mm, or may have a patterned area with some other suitable dimensions.

The patterned surface 22 may be provided with a single pattern, which for example forms a layer of a single integrated circuit. Alternatively, the patterned surface 22 may be provided with multiple patterns, which for example each form a layer of an integrated circuit. In an embodiment, the template may be sufficiently large to imprint a pattern onto the entire substrate during a single imprint.

The described and illustrated embodiment is to be considered as illustrative and not restrictive in character, it being understood that only a preferred embodiment has been shown and described and that all changes and modifications that come within the scope of the inventions as defined in the claims are desired to be protected.

Although FIG. 2a shows a particular apparatus according to an embodiment of the invention, other apparatus may be used. For example, the apparatus may be modified by placing the detector 14 in a different location. For example, the detector may be located adjacent where imprinting takes place such that the template may be inspected while held by a template holder used for imprinting of the substrate.

In an embodiment, the radiation source 23, detector 24, etc. may be moveable, and may be relocated away from the imprint template after inspection and optional cleaning have been completed. A moveable stage may be used to allow this movement to take place. Such relocation may allow UV radiation to be directed more easily onto the imprintable medium (for example if UV imprint lithography is being used).

In an embodiment, the substrate surface may be covered, for instance, with a top coat or a so-called BARC layer (Bottom Anti Reflection Coating). It is to be understood that the imprint template surface and/or substrate surface may not necessarily be completely flat or indeed planar (for instance the template surface may be slightly convex to assist with squeezing the imprint medium between the template surface and the substrate surface).

The present invention relates to an imprint lithography apparatus and method. The apparatus and/or method may be used for the manufacture of devices, such as electronic devices and integrated circuits or other applications, such as the manufacture of integrated optical systems, guidance and detection patterns for magnetic domain memories, flat-panel displays, liquid-crystal displays (LCDs), thin film magnetic heads, organic light emitting diodes, etc.

In this specification, the term "substrate" is meant to include any surface layers forming part of the substrate, or being provided on another substrate, such as a planarization layer or anti-reflection coating layer.

In this specification, the term "comprising" applied to a component means including that component, but not necessarily to the exclusion of other components. The term "consisting essentially" applied to one or more components means that other components other than impurities, or minor components not contributing to the technical effect of the invention, are substantially excluded. Typically this will mean that for a chemical composition, less than 5%, typically less than 1% by weight of other components will be present. For the avoidance of doubt, the use of the term "comprising" in this specification, in addition to the meaning set out above, also includes the narrower meaning of "consisting essentially".

In the above embodiments, a single imprint template, a single imprint template holder, a single substrate table and a single substrate is provided in a single chamber. In other embodiments, more than one imprint template, more than one imprint template holder, more than one substrate table, and/or more than one substrate may be provided in one or more chambers, in order for imprints to be undertaken more efficiently or quickly (e.g. in parallel). For example, in an embodiment, there is provided an apparatus that includes a plurality (e.g. 2, 3, or 4) of substrate tables. In an embodiment, there is provided an apparatus that includes a plurality (e.g. 2, 3, 4, 5, 6, 7 or 8 or more) of imprint templates. In an embodiment, there is provided an apparatus configured to use one template holder arrangement per substrate table. In an embodiment, there is provided an apparatus configured to use more than one template holder arrangement per substrate table. In an embodiment, there is provided an apparatus that includes a plurality (e.g. 2, 3, or 4) of imprintable medium dispensers. In an embodiment, there is provided an apparatus configured to use one imprintable medium dispenser per substrate table. In an embodiment, there is provided an apparatus configured to use one imprintable medium dispenser per imprint template arrangement. In an embodiment, where an apparatus is provided that includes a plurality of substrate tables, the substrate tables may share functionalities in the apparatus. For instance, the substrate tables may share a substrate handler, a substrate cassette, a gas supply system (e.g. to create a helium environment during imprinting), an imprintable medium dispenser, and/or a radiation source (for curing the imprintable medium). In an embodiment, two or more of the substrate tables (e.g. 3 or 4) share one or more functionalities of the apparatus (e.g. 1, 2, 3, 4, or 5 functionalities). In an embodiment, one or more functionalities (e.g. 1, 2, 3, 4, or 5) of the apparatus are shared among all substrate tables.

The invention claimed is:

1. A method of inspecting a patterned surface of an imprint template for use in imprint lithography of an imprintable medium on a substrate, wherein the imprintable medium or the imprint template comprises an anti-adhesion compound, the method comprising:
illuminating the patterned surface with radiation of a first wavelength such that fluorescence of defect particles of imprintable medium present on the patterned surface is induced to yield radiation of a second wavelength, and
using the radiation of the second wavelength as an indication of the presence of defect particles of imprintable medium on the patterned surface,
wherein the radiation of the first wavelength induces fluorescence of the radiation of the second wavelength from the imprintable medium and does not substantially induce fluorescence of radiation of the second wavelength from the anti-adhesion compound.

2. The method of claim 1, wherein the radiation of the first wavelength does not substantially induce fluorescence of radiation from the anti-adhesion compound.

3. The method of claim 1, comprising:
- detecting the radiation of the second wavelength with a detector; and
- transmitting a signal to a processor arranged to initiate cleaning of the patterned surface when the amount of radiation of the second wavelength detected by the detector exceeds a threshold value.

4. The method of claim 3, wherein a filter is positioned between the detector and the patterned surface, the filter arranged to permit passage of radiation of the second wavelength to the detector and prevent passage of radiation of the first wavelength to the detector.

5. The method of claim 1, wherein the anti-adhesion compound comprises a fluoroaliphatic polymeric ester.

6. The method of claim 1, wherein the first wavelength is 425 nm or greater.

7. The method of claim 1, wherein the imprintable medium comprises a UV-curable monomer and an initiator compound.

8. The method of claim 7, wherein the UV-curable monomer, when cured, exhibits fluorescence to emit radiation at the second wavelength when illuminated with radiation of the first wavelength.

9. The method of claim 7, wherein the UV-curable monomer comprises an acryloyl group.

10. The method of claim 7, wherein the initiator compound exhibits fluorescence of radiation at the second wavelength when illuminated with radiation of the first wavelength.

11. The method of claim 1, wherein the imprintable medium comprises a dye adapted to fluoresce radiation at the second wavelength when excited with radiation of the first wavelength.

12. The method of claim 1, wherein the imprintable medium comprises the anti-adhesion compound.

13. A method of detecting defect particles of imprintable medium on a patterned surface of an imprint template for imprint lithography of the imprintable medium on a substrate, the imprintable medium or the imprint template comprising an anti-adhesion compound, the method comprising illuminating the patterned surface with radiation of a first wavelength selected to induce fluorescence of the defect particles and not to induce fluorescence of anti-adhesion compound, wherein the presence of defect particles is indicated by the presence of fluorescence from the patterned surface.

14. The method of claim 13, wherein the anti-adhesion compound comprises a fluoroaliphatic polymeric ester.

15. The method of claim 13, wherein the imprintable medium comprises a UV-curable monomer and an initiator compound.

16. The method of claim 15, wherein the UV-curable monomer, when cured, exhibits fluorescence to emit radiation at the second wavelength when illuminated with radiation of the first wavelength.

17. The method of claim 15, wherein the initiator compound exhibits fluorescence of radiation at the second wavelength when illuminated with radiation of the first wavelength.

18. The method of claim 13, wherein the imprintable medium comprises a dye adapted to fluoresce radiation at the second wavelength when excited with radiation of the first wavelength.

19. The method of claim 13, wherein the imprintable medium comprises the anti-adhesion compound.

20. An imprint lithography template inspection apparatus comprising:
- an output of radiation of a first wavelength configured to illuminate a patterned surface of an imprint template;
- a detector assembly comprising a detector configured to detect the intensity of radiation of a second wavelength emitted from the patterned surface; and
- a processor configured to initiate cleaning of the patterned surface when the intensity of radiation of the second wavelength exceeds a threshold value, wherein the first wavelength is 425 nm or more and the second wavelength is greater than the first wavelength.

21. The apparatus of claim 20, further comprising a source of the radiation of the first wavelength.

22. An imprint lithography apparatus comprising the imprint lithography template inspection apparatus according to claim 20.

* * * * *